United States Patent [19]

Elliott et al.

[11] Patent Number: 5,905,062
[45] Date of Patent: *May 18, 1999

[54] CLEANSING COMPOSITIONS TECHNICAL FIELD

[75] Inventors: Russell Phillip Elliott, Egham; Matthew Thomas Green, Teddington; Christopher David Leahy, Kew Richmond; Eleni Papadimitriou, Putney, all of United Kingdom

[73] Assignee: The Procter & Gamble Company, Cincinnati, Ohio

[ * ] Notice: This patent is subject to a terminal disclaimer.

[21] Appl. No.: 08/849,425

[22] PCT Filed: Dec. 1, 1995

[86] PCT No.: PCT/US95/15722

§ 371 Date: Sep. 23, 1997

§ 102(e) Date: Sep. 23, 1997

[87] PCT Pub. No.: WO96/17916

PCT Pub. Date: Jun. 13, 1996

[30] Foreign Application Priority Data

Dec. 3, 1994 [GB] United Kingdom .................. 9424476

[51] Int. Cl.$^6$ ................ C11D 1/88; C11D 1/94; C11D 3/20

[52] U.S. Cl. .................. 510/124; 510/123; 510/125; 510/127; 510/137; 510/138; 510/159; 510/473; 424/70.12; 424/70.13; 424/70.15; 424/70.16; 424/70.19; 424/70.21; 424/70.22; 424/70.31; 514/846

[58] Field of Search ................ 510/137, 138, 510/159, 473, 123, 124, 125, 127; 424/70.12, 70.13, 70.15, 70.16, 70.19, 70.21, 70.22, 70.31; 514/846

[56] References Cited

U.S. PATENT DOCUMENTS

| 4,228,277 | 10/1980 | Landoll | 536/90 |
|---|---|---|---|
| 5,120,532 | 6/1992 | Wells et al. | 424/70 |
| 5,409,640 | 4/1995 | Giret et al. | 252/546 |
| 5,439,682 | 8/1995 | Wivell et al. | 724/401 |

*Primary Examiner*—Paul Lieberman
*Assistant Examiner*—Gregory R. Delcotto
*Attorney, Agent, or Firm*—Darryl C. Little; George W. Allen; T. David Reed

[57] ABSTRACT

A liquid personal cleansing composition comprising: a) from about 5% to about 60% by weight of water-soluble surfactant selected from anionic, nonionic and amphoteric surfactants and mixtures thereof; b) from about 0.01% to about 10% by weight of a hydrophobically modified nonionic cellulose ether selected from $C_{10}$–$C_{24}$ alkyl and alkenyl modified methyl, hydroxyethyl and hydroxypropyl cellulose ethers having a degree of nonionic substitution in the range of from about 1.8 to about 4 and a degree of hydrophobic substitution in the range of from about 0.1% to about 1% by weight; c) from about 0% to about 10% by weight of a water-soluble polyol; d) from about 0.01% to about 5% by weight of cationic polymeric skin conditioning agent; and e) water, and wherein the composition displays a shear stress of about 150 Pa at a shear rate in the range from about 100 s$^{-1}$ to about 600 s$^{-1}$ at 25° C. The products demonstrate excellent in-use efficacy benefits including mildness, a moisturised skin feel, desirable rheology and application characteristics, good rinsibility and good product stability.

19 Claims, No Drawings

CLEANSING COMPOSITIONS TECHNICAL FIELD

TECHNICAL FIELD

The present invention relates to cleansing compositions. In particular it relates to mild personal cleansing compositions with good skin feel attributes, rheological behaviour and foaming properties which are suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest are marginal in lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

In addition to the cleansing and lathering performance attributes desired by consumers it is of particular value that personal cleansing products further deliver certain in-use rheological properties. In particular a shower gel product which is capable of demonstrating shear thinning behaviour during application to the skin is preferred by consumers. It is known that water soluble polymers can be used to provide product thickening attributes and furthermore that hydrophobically modified water soluble polymers can exhibit enhanced product thickening behaviour and impart shear thinning characteristics. However it is also known that such product thickening/shear thinning effects are affected by the total surfactant level present in the system and in fact the thickening/thinning attributes can be significantly diminished in the presence of even very low levels of water soluble surfactants. A secondary effect of high surfactant and electrolyte concentration in systems containing hydrophobically modified water soluble polymers (HMWSPs) is that at increased surfactant levels the HMWSP can become increasingly insoluble in the product matrix.

Thus a need exists for personal cleansing products which deliver acceptable in-use skin feel characteristics but which will not dehydrate the skin or result in loss of skin suppleness, which will provide a level of skin conditioning performance in a wash and rinse-off product which previously has only been provided by a separate post-cleansing cosmetic moisturizer, which demonstrate desirable in-use rheology behaviour and which will produce a foam which is stable and of high quality, which are effective hair and skin cleansers, which have good rinsibility characteristics, and which at the same time have stable product and viscosity characteristics and remain fully stable under long term and stressed temperature storage conditions.

Nonionic water-soluble cellulose ethers are employed in a variety of applications, including hair care compositions. Widely used, commercially-available nonionic cellulose ethers include methyl cellulose, hydroxy propyl methyl cellulose, hydroxyethylcellulose, hydroxypropyl cellulose and ethyl hydroxyethyl cellulose.

Certain modified cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from 10 to 24 carbon atoms in an amount between 0.2 weight percent and the amount which renders said cellulose ether less than 1%, by weight, soluble in water. The cellulose ether to be modified is preferably one of low to medium molecular weight; i.e., less than 800,000 and preferably between 20,000 and 700,000 (75 to 2500 D.P.).

Modified cellulose ethers have been disclosed for use in a variety of composition types. Landoll ('277) teaches the use of certain materials in shampoo formulations. Hercules trade literature teaches the use of modified cellulose ethers materials in shampoos, liquid soaps, and lotions. U.S. Pat. No. 4,683,004 discloses the use of modified cellusoe ethers in mousse compositions for the hair. U.S. Pat. No. 4,485,089 teaches dentifrice compositions containing modified cellulose ethers.

It has now been found that personal cleansing compositions having improved skin feel and moisturisation attributes, both in use and after use, which deliver desirable thickening/thinning (rheology) benefits and good product stability can be formed by the combination of certain modified cellulose ethers, cationic polymers and surfactants. It has also been found that certain modified cellulose ethers having specified degrees of substitution and chain lengths confer particular benefits in personal cleansing compositions in terms of stability and application characteristics.

SUMMARY OF THE INVENTION

The subject of the present invention is a mild, foam-producing shear thinning, stable cleansing product suitable for personal cleansing of the skin or hair and which may be used as foam bath and shower products, skin cleansers and shampoos etc. According to one aspect of the invention, there is provided a liquid personal cleansing composition comprising:

(a) from about 5% to about 60% by weight of water-soluble surfactant selected from anionic, nonionic, zwitterionic and amphoteric surfactants and mixtures thereof;

(b) from about 0.01% to about 10% by weight of a hydrophobically modified nonionic cellulose ether selected from $C_{10}$–$C_{24}$ alkyl and alkenyl modified methyl, hydroxyethyl and hydroxypropyl cellulose ethers having a degree of nonionic substitution in the range of from about 1.8 to about 4 and a degree of hydrophobic substitution in the range of from about 0.1% to about 1% by weight;

(c) from about 0% to about 10% by weight of water-soluble polyol;

(d) from about 0.01% to about 5% by weight of cationic polymeric skin conditioning agent; and (e) water The composition preferably displays a shear stress of about 150 Pa at a shear rate in the range from about 100 $s^{-1}$ to about 600 $s^{-1}$ more preferably from about 400 $s^{-1}$ to about 600 $s^{-1}$ at 25° C.

According to another aspect of the invention there is provided a personal cleansing composition comprising:

a) from about 5% to about 60% by weight of water-soluble surfactant selected from anionic, nonionic and amphoteric surfactants and mixtures thereof;

(b) from about 0.01% to about 10% by weight of a hydrophobically modified nonionic cellulose ether selected from $C_{14}$–$C_{18}$ alkyl and alkenyl modified, hydroxyethyl cellulose ethers having a degree of nonionic substitution in the range of from about 2.2 to about 2.8 and a degree of hydrophobic substitution in the range of from about 0.4% to about 6% by weight; and (c) water.

Such composition preferably displays a shear stress of about 150 Pa at a shear rate in the range from about 400 $s^{-1}$ to about 600 $s^{-1}$ at 25° C.

In a highly preferred embodiment, the invention takes the form of a foam producing liquid cleansing composition with superior skin feel and rinsing characteristics, excellent rheological behaviour, improved perceived dryness and expertly graded dryness and skin hydration measurements and trans epidemal water loss (TEWL), combined with excellent lathering, good stability, cleansing ability and conditioning performance.

All concentrations and ratios herein are by weight of the cleansing composition, unless otherwise specified. Surfactant chain lengths are also on a weight average chain length basis, unless otherwise specified.

The liquid cleansing compositions herein are based on a combination of mild surfactants with certain hydrophobically modified cellulose ethers and polymeric skin conditioning agents. Preferred embodiments also contain perfume or cosmetic oils.

The compositions of the present invention contain, as an essential component, a hydrophobically modified cellulose ether as rheology modifying agent.

The cellulose ethers prior to hydrophobic modification have a degree of nonionic substitution in the range from about 1.8 to about 4.0, preferably from about 2 to about 3, and especially from about 2.2 to about 2.8. The cellulose ethers are then further substituted with alkyl or alkenyl groups having 10 to 24, preferably from about 14 to 18 carbon atoms in an amount from about 0.1 to about 1, preferably from about 0.3 to about 0.8, and especially from about 0.4 to about 0.6 weight percent. The cellulose ether to be modified is preferably one of low to medium molecular weight, i.e., less than 800,000 and preferably between 20,000 and 700,000 (75 to 2500 D.P.).

The preferred cellulose ether substrate is hydroxyethyl cellulose (HEC) of 50,000 to 700,000 molecular weight. Hydroxyethyl cellulose of this molecular weight level is the most hydrophilic of the materials completed. Accordingly, control of the modification process and control of the properties of the modified product can be more precise with this substrate. Hydrophilicity of the most commonly used nonionic cellulose ethers varies in the general direction: hydroxyethyl>hydroxypropyl>hydroxypropyl methyl>methyl.

The long chain alkyl modifier can be attached to the cellulose ether substrate via an ether, ester or urethane linkage. The ether linkage is preferred. Although the modified cellulose ether materials are referred to as being "alkyl modified", (the term alkyl as used generally herein also includes using alkenyl) it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. General methods for making modified cellulose ethers are taught in Landoll ('277) at column 2, lines 36–65.

Modified cellulose ethers of defined substitution levels and hydrophobic chain length have been found to be particularly desirable for use as rheology modifiers in the personal cleansing compositions of the present invention. The materials are able to stabilize suspension of dispersed phases, and when used with the additional components in the compositions of the present invention, they produce rheologically thick products which display desirable shear thinning behaviour in-use. In addition, the combination of hydrophobically modified cellulose ethers with cationic polymeric skin conditioning agents have also been found to be particularly beneficial from the viewpoint of viscosity enhancement combined with shear-thinning behaviour during application to the skin or hair.

The rheology modifying agents for use herein are selected from hydrophobically modified water-soluble polymers and in particular from hydrophobically modified hydroxy ethyl cellulose polymers. Suitable hydrophobically modified hydroxy ethyl cellulose (HMHEC) polymers have a 1% aqueous viscosity in the range of from about 8,000 to about 13,000 mPas (Brookfield LVT viscometer, spindle No. 4, speed 4).

One commercially available material suitable for use herein is NATROSOL PLUS Grade 330 CS (RTM), a hydrophobically modified hydroxyethylcellulose available from Aqualon Company, Wilmington, Del. This material has a $C_{16}$ alkyl substitution of from 0.4% to 0.8% by weight. The hydroxyethyl molar substitution for this material is from 3.0 to 3.7. The average molecular weight for the water-soluble cellulose prior to modification is approximately 300,000.

Another material of this type is sold under the trade name NATROSOL PLUS CS Grade D-67 (RTM), by Aqualon Company, Wilmington, Del. This material has a $C_{16}$ substitution of from 0.50% to 0.95%, by weight. The hydroxyethyl molar substitution for this material is from 2.3 to 3.7. The average molecular weight for the water soluble cellulose prior to modification is approximately 700,000.

Preferred for use herein are $C_{14}$–$C_{18}$ alkyl and alkenyl modified hydroxy ethyl cellulose polymers having a degree of ethoxylation of from about 1.8 to about 3.2, preferably from about 2.0 to about 3.0, more preferably from about 2.2 to about 2.8 and an alkyl and alkenyl substitution level of from about 0.3 to about 0.8, preferably from about 0.4 to about 0.6. Highly preferred are cetyl modified hydroxy ethyl cellulose polymers as available from the Aqualon Co. under the trade names Polysurf 67 (RTM).

The hydrophobically modified cellulose ether is preferably present at a level of from about 0.02% to about 5%, more preferably from about 0.05% to about 1%, and especially from about 0.1% to about 0.5% by weight.

The modified cellulose ethers herein are particularly valuable for providing excellent stability characteristics over normal temperatures as well as delivering shear thinning behaviour in a high surfactant matrix and for delivery of improved rheological behaviour in combination with the selected cationic polymeric skin conditioning agents.

The compositions according to the present invention are shear thinning and preferably display a shear stress of about 150 Pa at a shear rate in the range of from about 100 s$^{-1}$ to about 600 s$^{-1}$ at 25° C. Highly preferred compositions display a shear stress of about 150 Pa at a shear rate in the range from about 400 s$^{-1}$ to about 600 s$^{-1}$ at 25° C. (as measured using a Carri-Med CSL 100 Rheometer with a spindle of cone 4 cm and 2 degrees 49 micron truncation).

Neutralizing agents suitable for use in neutralizing acidic group containing rheology modifying agents described herein include sodium hydroxide, potasssium hydroxide, ammonium hydroxide, monoethanolamine, diethanolamine and triethanolamine and mixtures thereof.

The compositions according to the present invention also preferably include a skin conditioning cationic polymer. The cationic polymer is valuable in the compositions according to the present invention for provision of skin feel attributes and for improved rheology and application characteristics in the presence of the hydrophobically modified cellulose ether moiety. The polymeric skin conditioning agent is preferably present at a level from about 0.01% to about 5%, preferably from about 0.05% to about 3% and especially from about 0.1% to about 2% by weight.

Suitable polymers are high molecular weight materials (mass-average molecular weight determined, for instance, by light scattering, being generally from about 2,000 to about 5,000,000, preferably from about 5,000 to about 3,000,000 more preferably from 100,000 to about 1,000,000).

Representative classes of polymers include cationic polysaccharides; cationic homopolymers and copolymers derived from acrylic and/or methacrylic acid; cationic cellulose resins; cationic copolymers of dimethyldiallylammonium chloride and acrylamide and or acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16 (RTM), which contains hydroxypropyl substituents (d.s. of from 0.8–1.1) in addition to the above-specified cationic groups, and quaternized cellulose ethers available commercially under the trade names Ucare Polymer JR-30M, JR400, Catanal (RTM) and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, acrylic acid/dimethyldiallylammonium chloride/acrylamide copolymers available under the trade name Merquat 3300, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and HS-100), vinyl pyrrolidone/vinyl imidazolium methochloride copolymers available under the trade names Luviquat HM552, Polyquaternium 2, and polyalkyleneimines such as polyethylenimine and ethoxylated polyethylenimine.

The present compositions can also comprise a nonionic or anionic polymeric thickening component, especially a water-soluble polymeric materials, having a molecular weight greater than about 20,000. By "water-soluble polymer" is meant that the material will form a substantially clear solution in water at a 1% concentration at 25° C. and the material will increase the viscosity of the water. Examples of water-soluble polymers which may desirably be used as an additional thickening component in the present compositions, are hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan. Preferred as the additional thickeners for the present compositions are natural polysaccharide materials. Examples of such materials are guar gum, locust bean gum, and xanthan gum. Also suitable herein preferred is hydroxyethyl cellulose having a molecular weight of about 700,000.

Additional polymeric thickening agents include acrylic acid/ethyl acrylate copolymers and the carboxyvinyl polymers sold by the B. F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified crosslinked polymers of acrylic acid having amphipathic properties available under the Trade Name Carbopol 1382, Carbopol 1342 and Pemulen TR-1 (CFTA Designation: Acrylates/10-30 Alkyl Acrylate Crosspolymer). A combination of the polyalkenyl polyether cross-linked acrylic acid polymer and hydrophobically modified cross-linked acrylic acid polymer is also suitable for use herein.

The polymeric thickening component, if present in the compositions of the present invention, is at a level of from 0.3% to 5.0%, preferably from 0.4% to 3.0% by weight.

Further additional thickening agents suitable for use herein include ethylene glycol or polyethylene glycol esters of a fatty acid having from about 16 to about 22 carbon atoms and up to 7 ethyleneoxy units, preferably the ethylene glycol stearates, both mono and distearate, but particularly the distearate containing less than about 7% of the mono stearate, alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide, alkyl ($C_{16}$–$C_{22}$) dimethyl amine oxides such as stearyl dimethyl amine oxide and electrolytes such as magnesium sulphate and sodium chloride salts.

A preferred feature of the compositions of the present invention is a solubilising agent for the hydrophobically modified cellulose ether. The solubilising agent is valuable for limiting aggregation of cellulose ether possibly via interaction around the hydrophobic pendant chains on the polymeric moieties. The solubilising agent is preferably present at a level of from about 0.1% to about 10%, more preferably from about 0.5% to about 5%, and especially from about 1% to about 4% by weight. The ratio of hydrophobically modified cellulose ether to solubilising agent is in the range of from about 0.1:10 to about 0.2:5, preferably from about 0.3:5 to about 0.4:1.

Suitable solubilising agents include water-soluble polyols. Preferred are water soluble polyols having molecular weights of from about 40 to about 2000, more preferably from about 50 to about 500 and especially from about 58 to about 200 and multiple hydroxyl groups. Multiple hydroxyl groups as defined herein means from about 2 to about 6 hydroxyl groups. Water-soluble polyols suitable for inclusion herein as solubilising agents are selected from glycerin, propylene glycol, hexylene glycol, mannitol, polyethylene glycol, sorbitol, polyethylene glycol and propylene glycol ethers of methyl glucose (e.g. ethyl glucam E-20 and propylglucam P-10), polyethylene glycol and propylene glycol ethers of lanolin alcohol (e.g. Solulan-75) and mixtures thereof. Highly preferred solubilising agents for use herein are glycerin and propylene glycol.

Mild surfactants suitable for inclusion in compositions according to the present invention can be selected from anionic, nonionic, amphoteric and zwitterionic surfactants and mixtures thereof. The total level of surfactant is preferably from about 5% to about 60%, more preferably from about 6% to about 40%, and especially from about 8% to about 35% by weight. The compositions preferably comprise a mixture of anionic with zwitterionic and/or amphoteric surfactants. The level of the individual anionic, zwitterionic and amphoteric surfactant components, where present, is in the range from about 1% to about 15%, and especially from about 2% to about 13% by weight of the composition, while the level of nonionic surfactant, where present, is in the range from about 0.1% to about 20% by weight, preferably from about 0.5% to about 16%, more preferably from about 1% to about 12% by weight. The weight ratio of anionic surfactant: zwitterionic and/or amphoteric surfactant is in the range from about 1:2 to about 6:1. Other suitable compositions within the scope of the invention comprise mixtures of anionic, zwitterionic and/or amphoteric surfactants with one or more nonionic surfactants. Preferred for use herein are soluble or dispersible nonionic surfactants selected from ethoxylated animal and vegetable oils and fats and mixtures thereof, sometimes referred to herein as "oil-derived" nonionic surfactants.

Anionic surfactants suitable for inclusion in the compositions of the invention can generally be described as mild synthetic detergent surfactants and include ethoxylated alkyl sulfates, alkyl glyceryl ether sulfonates, methyl acyl taurates, fatty acyl glycinates, N-acyl glutamates, acyl isethionates, alkyl sulfosuccinates, alpha-sulfonated fatty acids, their salts and/or their esters, alkyl ethoxy carboxylates, alkyl phosphate esters, ethoxylated alkyl phosphate esters, acyl sarcosinates and fatty acid/protein condensates, and mixtures thereof. Alkyl and/or acyl chain lengths for these surfactants are $C_8$–$C_{22}$, preferably $C_{10}$–$C_{18}$ more preferably $C_{12}$–$C_{14}$.

Preferred for use herein from the viewpoint of optimum mildness and lathering characteristics are the salts of sulfuric acid esters of the reaction product of 1 mole of a higher fatty alcohol and, from about 1 to about 12 moles of ethylene oxide, with sodium and magnesium being the preferred counterions. Particularly preferred are the alkyl sulfates containing from about 2 to 6, preferably 2 to 4 moles of ethylene oxide, such as sodium laureth-2 sulfate, sodium laureth-3 sulfate and magnesium sodium laureth-3.6 sulfate. In preferred embodiments, the anionic surfactant contains at least about 50%, especially at least about 75% by weight of ethoxylated alkyl sulfate.

The compositions for use herein suitably also contain an amphoteric surfactant. Amphoteric surfactants suitable for use in the compositions of the invention include:

(a) imidazolinium surfactants of formula (I)

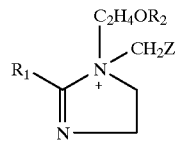

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (II)

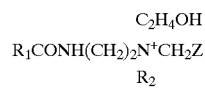

wherein $R_1$, $R_2$ and Z are as defined above;

(b) aminoalkanoates of formula (III)

iminodialkanoates of formula (IV)

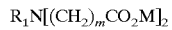

and iminopolyalkanoates of formula (V)

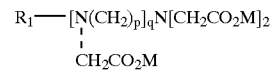

wherein n, m, p, and q are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula I, although the CTFA Cosmetic Ingredient Dictionary, 3rd Edition indicates the non-cyclic structure 11 while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula I and/or II in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

The compositions herein can also contain from about 0.1% to about 20%, more preferably from about 0.1% to about 10%, and especially from about 1% to about 8% of a zwitterionic surfactant.

Betaine surfactants suitable for inclusion in cleansing compositions include alkyl betaines of the formula $R_5R_6R_7N^+$ $(CH_2)_nCO_2M(VI)$ and amido betaines of the formula (VII)

$$R_5CON(CH_2)_mN(CH_2)_nCO_2M$$
$$\underset{R_7}{\overset{R_6}{|}}$$

wherein $R_5$ is $C_{12}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine.

The compositions of the invention preferably also contain from about 0.1% to about 20%, preferably from about 1% to about 15%, and more preferably from about 2% to about 10% by weight of an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula (VIII)

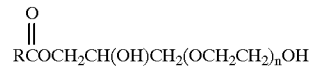

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived nonionic surfactants of this class are available from Croda Inc. (New York, USA) under their Crovol line of materials such as Crovol EP40 (PEG 20 evening primrose glyceride), Crovol EP 70 (PEG 60 evening primrose glyceride) Crovol A-40 (PEG 20 almond glyceride), Crovol A-70 (PEG 60 almond glyceride), Crovol M-40 (PEG 20 maize glyceride), Crovol M-70 (PEG 60 maize glyceride), Crovol PK-40 (PEG 12 palm kernel glyceride), and Crovol PK-70 (PEG 45 palm kernel glyceride) and under their Solan range of materials such as Solan E, E50 and X polyethoxylated lanolins and Aqualose L-20 (PEG 24 lanolin alcohol) and Aqualose W15 (PEG 15 lanolin alcohol) available from Westbrook Lanolin. Further suitable surfactants of this class are commercially available from Sherex Chemical Co. (Dublin, Ohio, USA) under their Varonic LI line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates). Other oil-derived emollients suitable for use are PEG derivatives of corn, avocado, and babassu oil, as well as Softigen 767 (PEG(6) caprylic/capric glycerides).

Also suitable for use herein are nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sederma (78610 Le Perray En Yvelines, France). Particularly suitable are ethoxylated derivatives of Shea butter available from Karlshamn Chemical Co. (Columbos, Ohio, USA) under their Lipex range of chemicals, such as Lipex 102 E-75 and Lipex 102 E-3 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazlenut oil, olive oil, grapeseed oil, and sunflower seed oil.

Oil derived nonionic surfactants highly preferred for use herein from the viewpoint of optimum mildness and skin feel characteristics are Lipex 102-3 (RTM) (PEG-3 ethoxylated derivatives of Shea Butter) and Softigen 767 (RTM) (PEG-6 caprylic/capric glycerides).

In addition to the above oil derived nonionic surfactants, the compositions of the invention can also comprise an auxiliary nonionic surfactant at levels from about 0.1% to about 20%, more preferably from about 0.1% to about 10%, and especially from about 1% to about B% by weight. Surfactants of this class include C12–C14 fatty acid mono- and diethanolamides, sucrose polyester surfactants and polyhydroxy fatty acid amide surfactants having the general formula (IX).

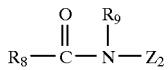

The preferred N-alkyl, N-alkoxy or N-aryloxy, polyhydroxy fatty acid amide surfactants according to formula (IX) are those in which $R_8$ is $C_5$–$C_{31}$ hydrocarbyl, preferably $C_9$–$C_{17}$ hydrocarbyl, including straight-chain and branched chain alkyl and alkenyl, or mixtures thereof and $R_9$ is typically $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH$—$CH_2OH$, where n is an integer from 1 to 5, inclusive, and R' is H or a cyclic mono- or poly-saccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C7–C17 straight chain alkyl or alkenyl group.

In compounds of the above formula, $R_8CO$—N< can be, for example, cocoamide, stearamide, oleamide, lauramide, myristamide, capricamide, palmiamide, tallowamide, etc.

A preferred process for making the above compounds having formula (IX) comprises reacting a fatty acid triglyceride with an N-substituted polyhydroxy amine in the substantial absence of lower ($C_1$–$C_4$) alcoholic solvent, but preferably with an alkoxylated alcohol or alkoxylated alkyl phenol such as NEODOL and using an alkoxide catalyst at temperatures of from about 50° C. to about 140° C. to provide high yields (90–98%) of the desired products.

The compositions of the invention may also include an insoluble perfume or cosmetic oil or wax or a mixture thereof at a level up to about 10%, preferably up to about 3% by weight wherein the oil or wax is insoluble in the sense of being insoluble in the product matrix at a temperature of 25° C. Addition of such oils or waxes can provide emolliency, mildness and rinsibility characteristics to personal cleansing compositions according to the invention. It is a feature of the invention, however, that compositions having excellent emolliency and mildness together with desirable physical attributes (clarity etc.) can be delivered which are essentially oil-free, ie which contain less than about 1%, preferably less than 0.5% by weight of an added oil phase. Physically, preferred compositions of this type take the form of an optically-clear solution or microemulsion. In compositions including an additional perfume or cosmetic oil or wax, preferably the weight ratio of oil-derived nonionic surfactant to added oil is at least about 1:2, more especially at least about 3:1.

Suitable insoluble cosmetic oils and waxes for use herein can be selected from water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate, myristyl myristate and cetyl ricinoleate, $C_8$–$C_{30}$ esters of benzoic acid, beeswax, saturated and unsaturated fatty alcohols such as behenyl alcohol, hydrocarbons such as mineral oils, petrolatum squalane and squalene, polybutene, fatty sorbitan esters (see U.S. Pat. No. 3,988,255, Seiden, issued Oct. 26th 1976), lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazlenut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate.

The viscosity of the final composition (Brookfield RVT DCP, 1 rpm with Cone CP41 or CP52, 25° C., neat) is preferably at least about 500 cps, more preferably from about 1,000 to about 50,000 cps, especially from about 4,000 to about 30,000 cps, more especially from about 4,000 to about 15,000 cps.

The cleansing compositions can optionally include other hair or skin moisturizers which are soluble in the cleansing composition matrix. The preferred level of such moisturizers is from about 0.5% to about 20% by weight. In preferred embodiments, the moisturizer is selected from essential amino acid compounds found naturally occurring in the stratum corneum of the skin and water-soluble nonpolyol nonocclusives and mixtures thereof.

Some examples of more preferred nonocclusive moisturizers are polybutene, squalane, sodium pyrrolidone carboxylic acid, lactic acid, L-proline, guanidine, pyrrolidone, hydrolyzed protein and other collagen-derived proteins, aloe vera gel, acetamide MEA and LMEA and mixtures thereof.

Compositions according to the present invention may also include an opacifier or pearlescing agent. Such materials may be included at a level of from about 0.01% to about 5%, preferably from about 0.2% to about 1.3% by weight. A suitable opacifier for inclusion in the present compositions is a polystyrene dispersion available under the trade names Lytron 621 & 631 (RTM) from Morton International.

Additional opacifiers/pearlescers suitable for inclusion in the compositions of the present invention include: titanium dioxide, $TiO_2$; EUERLAN 810 (RTM); TEGO-PEARL (RTM); long chain ($C_{16}$–$C_{22}$) acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl ($C_{16}$–$C_{22}$) dimethyl amine oxides such as stearyl dimethyl amine oxide.

In preferred compositions the opacifier/pearlescer is present in the form of crystals. In highly preferred compositions the opacifier/pearlescer is a particulate polystyrene dispersion having a particle size of from about 0.05 microns to about 0.45 microns, preferably from about 0.17 microns to about 0.3 microns, such dispersions being preferred from the viewpoint of providing optimum rheology and shear-thinning behaviour. Highly preferred is styrene PVP copolymer and Lyton 631 (RTM).

A number of additional optional materials can be added to the cleansing compositions each at a level of from about 0.1% to about 2% by weight. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663; solvents; anti-bacterial agents such as Oxeco (phenoxy isopropanol); low temperature phase modifiers such as ammonium ion sources (e.g. $NH_4$ Cl); viscosity control agents such as magnesium sulfate and other electrolytes; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. Water is also present at a level preferably of from about 15% to about 94.98%, preferably from about 40% to about 90%, more preferably at least about 65% by weight of the compositions herein.

The pH of the compositions is preferably from about 4 to about 10, more preferably from about 6 to about 9, especially from about 5 to about 6.

The invention is illustrated by the following non-limiting examples.

In the examples, all concentrations are on a 100% active basis and the abbreviations have the following designation:

| | |
|---|---|
| Amphoteric | Cocoamphodiacetate |
| Anionic 1 | Sodium laureth-3 sulfate |
| Anionic 2 | Sodium lauroyl sarcosinate |
| Nonionic | PEG-3 Shea butter |
| Crovol | Crovol EP 70 (PEG 60 evening primrose triglycerides) |
| GA | Polyhydroxy fatty acid amide of formula IX in which $R_8$ is $C_{11}$–$C_{17}$ alkyl, $R_9$ is methyl, and $Z_2$ is $CH_2(CHOH)_4CH_2OH$ |
| HMHEC | Cetyl modified hydroxyethylcellulose having a nonionic substitution of from about 0.4 to about 0.6 and a degree of ethoxylation of from about 2.2 to about 2.8 - Polysurf 67 (RTM). |
| Polymer 1 | Polymer JR-30(RTM) - hydroxyethylcellulose reacted with epichlorohydrin and quaternized with trimethylamine, m. wt. $4 \times 10^6$ |
| Polymer 2 | Gafquat 755N |
| Preservative | Phenoxyethanol/sodium benzoate/EDTA (4:2:1) |
| Pearlescer | Ethyleneglycoldistearate/emulsifier mixture |
| Opacifier | Lytron 631 (RTM) |
| Oil | Soyabean Oil |
| Softigen 767 | PEG(6) caprylic/capric glycerides |

EXAMPLES I TO VI

The following are personal cleansing compositions in the form of shower gel or bath foam products and which are representative of the present invention:

| | I | II | III | IV | V | VI |
|---|---|---|---|---|---|---|
| Amphoteric | 3.0 | 3.0 | — | 5.0 | — | 4.0 |
| Anionic 1 | 6.0 | 6.0 | 13.0 | 10.0 | 6.0 | 4.0 |
| Anionic 2 | 1.0 | 2.0 | 2.0 | 2.0 | 1.0 | — |
| GA | 3.0 | — | — | 3.0 | 3.0 | — |
| Oil | — | 4.0 | — | 6.0 | 4.0 | — |
| Softigen 767 | — | 1.0 | — | 2.0 | 2.0 | — |
| Nonionic | — | 0.4 | — | 1.0 | — | 0.3 |
| Crovol | — | — | 1.0 | — | — | 3.0 |
| HMHEC | 0.3 | 0.4 | 0.5 | 0.1 | 0.3 | 0.35 |
| Polymer 1 | 0.8 | 1.0 | — | 0.2 | 0.8 | — |
| Polymer 2 | — | — | 0.5 | — | — | 0.2 |
| Glycerine | 1.0 | 3.0 | 1.0 | 2.0 | 1.5 | 5.0 |
| Pearlescer | — | — | — | 3.0 | 1.0 | 1.0 |
| Opacifier | 0.2 | 0.3 | 0.4 | — | — | — |
| Preservative | 0.5 | 0.5 | 0.5 | 1.0 | 1.0 | 1.0 |
| Perfume | 1.0 | 1.0 | 1.0 | 1.0 | 1.0 | 1.0 |
| Zinc Stearate | — | — | 0.8 | — | — | 1.0 |
| Water | | | to 100 | | | |

Compositions I to VI are prepared by firstly dispersing the water-soluble or colloidally water-soluble polymeric rheology modifier in water at 25° C. either in a Tri-blender (RTM) or by extended stirring prior to neutralisation with NaOH or alternative base mixture and hydration. In examples II, IV and VI the mixture can be heated to about 50° C. to enhance dispersion efficiency. Next the solubilisation agent is added with further stirring. The surfactants and other skin care agents can then be added along with the remaining water-soluble, oil-insoluble ingredients. In compositions which comprise water-insoluble ingredients an oil phase B is formed from these oil-soluble ingredients which is then admixed with A at ambient temperature. The polymeric dispersion is then added to the ambient temperature mix and finally the remaining water, preservative, opacifier and perfume are added.

The products provide excellent in-use and efficacy benefits including mildness, skin conditioning, skin moisturising, stability, rheology, application characterisitcs, cleansing, lathering and rinsibility.

What is claimed is:

1. A liquid personal cleansing composition comprising:
   A.) a rheology regulating composition, comprising:
      a.) from about 5% to about 60% by weight of water-soluble surfactant selected from anionic, nonionic, zwitterionic and amphoteric surfactants and mixtures thereof; and b.) from about 0.01% to about 10% by weight of a hydrophobically modified nonionic cellulose ether selected from $C_{10}$–$C_{24}$ alkyl and alkenyl modified methyl, hydroxyethyl and hydroxy propyl cellulose ethers having a degree of nonionic substitution in the range of from about 1.8 to about 4 and a degree of hydrophobic substitution in the range of from about 0.1% to about 1% by weight;

c.) from about 0 to about 10% by weight of a water-soluble polyol; and d.) from about 0.01% to about 5% by weight of cationic polymeric skin conditioning agent selected from the group consisting of cationic guar gums, homopolymers of dimethyldiallylammonium chloride, copolymers of dimethyl aminoethylmethacrylate and acrylamide, copolymers of dimethyldialkylammonium chloride and acrylamide, acrylic acid/dimethyldiallylammonium chloride/acrylamide terpolymers, quaternized vinyl pyrrolidone acrylate or methacrylate copolymers of amino alcohol, vinyl pyrrolidone/vinyl imidazolium methochloride copolymers, polyalkyleneimines and mixtures thereof; and B.) water and wherein the composition displays a shear stress of about 150 Pa at a shear rate in the range form about 100 $s^{-1}$ to about 600 $s^{-1}$ at 25° C.

2. A composition according to claim 1 wherein the hydrophobically modified cellulose ether is selected from hydroxyethylcellulose derivatives having a degree of nonionic substitution in the range of from about 2.0 to about 3.0 and a degree of hydrophobic substitution in the range of from about 0.3% to about 0.8% by weight.

3. A composition according to claim 2 wherein the hydrophobically modified cellulose ether is selected from $C_{14}$–$C_{18}$ alkyl and alkenyl modified hydroxy ethyl celluloses having a degree of nonionic subsitution in the range of from about 2.2 to about 2.8 and a degree of hydrophobic substitution in the range of from about 0.4 to about 0.6.

4. A composition according to claim 1 wherein the water soluble polyol has a molecular weight of from about 40 to about 200 and from about 2 to about 6 hydroxyl groups.

5. A composition according to claim 4 wherein the water-soluble polyol is selected from the group consisting of glycerin, propylene glycol, polyethylene glycol, polypropylene glycol, sorbitol and mixtures thereof.

6. A composition according to claim 1 wherein the composition has a viscosity (Brookfield RVT DCP, 1 rpm with Cone CP41 or CP52, 25° C., neat) in the range from 1,000 to 50,000 cps.

7. A composition according to claim 1 wherein the polymeric skin conditioning agent has a mass average molecular weight in the range from about 2000 to about 5,000,000.

8. A composition according to claims 1 comprising a mixture of anionic with zwitterionic and/or amphoteric surfactants and wherein the level of the individual anionic, zwitterionic and amphoteric surfactant components is in the range from about 1% to 15% by weight.

9. A composition according to claim 8 comprising from about 0.1% to about 20% by weight of nonionic surfactant selected from the group consisting of ethoxylated oils and fats having the formula (VIII)

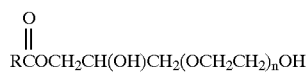

wherein n is from about 5 to 200, and wherein R comprises an aliphatic radical having an average from about 5 to 20 carbon atoms, and mixtures thereof.

10. A composition according to claim 8 wherein the anionic surfactant is selected from the group consisting of ethoxylated alkyl sulfates, alkyl glyceryl ether sulfonates, methyl acyl taurates, fatty acyl glycinates, alkyl ethoxy carboxylates, N-acyl glutamates, acyl isethionates, alkyl sulfosuccinates, alpha-sulfonated fatty acids, their salts and/or their esters, alkyl phosphate esters, ethoxylated alkyl phosphate esters, acyl sarcosinates and fatty acid/protein condensates, and mixtures thereof.

11. A composition according to claim 10 wherein the anionic surfactant comprises an ethoxylated $C_8$–$C_{22}$ alkyl sulfate.

12. A composition according to claim 8 wherein the amphoteric surfactant is selected from the group consisting of (a) imidazolinium derivatives of formula [I]

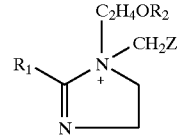

wherein $R_1$ is $C_7$–$C_{22}$ alkyl or alkenyl, $R_2$ is hydrogen of $CH_2Z$, each Z is independently $CO_2$ or $CH_2$ $CO_2M$, and M is H, alkali metal, alkaline earth metal, ammonium or alkanolammonium; and/or ammonium derivatives of formula [II]

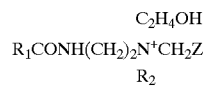

wherein $R_1$, $R_2$ and Z are as defined above:

(b) aminoalkanoates of formula [III]

iminodialkanoates of formula [IV]

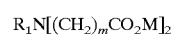

and iminopolyalkanoates of formula (V)

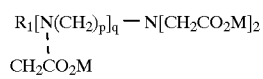

wherein n, m, p, and q are numbers from 1 to 4, and $R_1$ and M are independently selected from the groups specified above; and (c) and mixtures thereof.

13. A composition according to claim 12 wherein the amphoteric is selected from the group consisting of imidazolinium derivatives of formula I, ammonium derivatives of formula II, and mixtures thereof.

14. A composition according to claim 12 wherein the weight ratio of anionic surfactant:zwitterionic and/or amphoteric surfactant is in the range of from about 1:2 to about 6:1.

15. A composition according to claim 14 wherein the anionic, zwitterionic and amphoteric surfactants together comprise from about 8% to about 35%, preferably from about 10% to about 30% by weight of the composition.

16. A composition according to claim 10 which additionally comprises from about 0.1% to about 20% by weight of an auxiliary nonionic surfactant selected from $C_{12}$–$C_{14}$ fatty acid mono-and diethanolamides and polyhydroxy fatty acid amide surfactants.

17. A composition according to claim 9 which additionally comprises from about 0.1% to about 20% by weight of an auxiliary nonionic surfactant selected from $C_{12}$–$C_{14}$ fatty acid mono-and diethanolamides and polyhydroxy fatty acid amide surfactants.

18. A composition according to claim 1 additionally comprising up to about 20% by weight of perfume or cosmetic oil.

19. A composition according to claim 1 additionally comprising moisturiser selected from the group consisting of sodium pyrrolidone carboxylic acid, L-proline and mixtures thereof.

* * * * *